(12) United States Patent
Bogue et al.

(10) Patent No.: US 10,947,033 B2
(45) Date of Patent: *Mar. 16, 2021

(54) REDUCTION IN STRESS CRACKING OF FILMS

(71) Applicant: Aquestive Therapeutics, Inc., Warren, NJ (US)

(72) Inventors: Beuford Arlie Bogue, Valparaiso, IN (US); Greg Slominski, Valparaiso, IN (US)

(73) Assignee: Aquestive Therapeutics, Inc., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/662,566

(22) Filed: Oct. 24, 2019

(65) Prior Publication Data

US 2020/0122920 A1   Apr. 23, 2020

Related U.S. Application Data

(60) Continuation of application No. 15/710,260, filed on Sep. 20, 2017, now Pat. No. 10,464,739, which is a
(Continued)

(51) Int. Cl.
*B65D 85/67* (2006.01)
*B32B 1/02* (2006.01)
(Continued)

(52) U.S. Cl.
CPC ............ *B65D 85/67* (2013.01); *A61J 1/035* (2013.01); *B32B 1/02* (2013.01); *B32B 27/08* (2013.01); *B32B 27/308* (2013.01); *B32B 27/32* (2013.01); *B32B 27/36* (2013.01); *B65B 7/02* (2013.01); *B65B 9/04* (2013.01); *B65B 9/045* (2013.01); *B65B 11/50* (2013.01); *B65D 65/38* (2013.01); *B65D 81/18* (2013.01); *B65D 85/54* (2013.01); *A61K 9/7007* (2013.01); *B32B 2250/02* (2013.01); *B32B 2250/24* (2013.01);
(Continued)

(58) Field of Classification Search
CPC ........... B65B 9/04; B65B 9/045; B65B 11/50; B65D 85/54; B65D 85/67; B32B 1/02; Y10T 428/1352
See application file for complete search history.

(56) References Cited

U.S. PATENT DOCUMENTS 2,615,754 A   10/1952 Lindenberg
3,928,700 A   12/1975 Lupica
(Continued)

FOREIGN PATENT DOCUMENTS

EP   0 688 812 A1   12/1995
EP   2 354 034 A1   8/2011

OTHER PUBLICATIONS

International Search Report issued to PCT/US2014/028266, dated Jul. 7, 2014.
Written Opinion issued to PCT/US2014/028266, dated Jul. 7, 2014.

*Primary Examiner* — Walter Aughenbaugh
(74) *Attorney, Agent, or Firm* — Hoffmann & Baron, LLP

(57) ABSTRACT

Methods and packages for storing film strips while reducing or eliminating stress cracking during storage, including use of packages having an inner surface made from polymeric materials exhibiting various physical properties and including films and pouches that are annealed.

20 Claims, 4 Drawing Sheets

Related U.S. Application Data continuation of application No. 15/160,606, filed on May 20, 2016, now Pat. No. 9,771,173, which is a division of application No. 13/844,423, filed on Mar. 15, 2013, now Pat. No. 9,346,601.

(51) Int. Cl.

| | |
|---|---|
| *B65D 81/18* | (2006.01) |
| *B65D 85/00* | (2006.01) |
| *B65B 9/04* | (2006.01) |
| *B65B 11/50* | (2006.01) |
| *B32B 27/08* | (2006.01) |
| *B32B 27/32* | (2006.01) |
| *A61J 1/03* | (2006.01) |
| *B32B 27/30* | (2006.01) |
| *B32B 27/36* | (2006.01) |
| *B65B 7/02* | (2006.01) |
| *B65D 65/38* | (2006.01) |
| *A61K 9/70* | (2006.01) |

(52) U.S. Cl.
CPC ... *B32B 2307/538* (2013.01); *B32B 2307/728* (2013.01); *B32B 2439/80* (2013.01); *Y10T 428/1352* (2015.01)

(56) References Cited

U.S. PATENT DOCUMENTS

| | | | |
|---|---|---|---|
| 4,416,791 A * | 11/1983 | Haq | C11D 17/042 510/296 |
| 5,024,842 A | 6/1991 | Edgren et al. | |
| 5,662,928 A | 9/1997 | Braun | |
| 5,789,046 A | 8/1998 | Mueller | |
| 6,708,826 B1 | 3/2004 | Ginsberg et al. | |
| 7,666,337 B2 * | 2/2010 | Yang | A61K 8/0216 264/172.19 |
| 2003/0107149 A1 | 6/2003 | Yang et al. | |
| 2006/0023976 A1 | 2/2006 | Alvater et al. | |
| 2007/0170196 A1 | 7/2007 | Libohova et al. | |
| 2008/0242736 A1 | 10/2008 | Fuisz | |
| 2012/0076921 A1 | 3/2012 | Myers et al. | |

* cited by examiner

REDUCTION IN STRESS CRACKING OF FILMS

CROSS REFERENCE TO RELATED APPLICATIONS

The present application is a continuation of U.S. application Ser. No. 15/710,260, filed Sep. 20, 2017, now U.S. Pat. No. 10,464,739 B2, which is a continuation of U.S. application Ser. No. 15/160,606, filed on May 20, 2016, now U.S. Pat. No. 9,771,173 B2, which is a divisional of U.S. application Ser. No. 13/844,423, filed on Mar. 15, 2013, now U.S. Pat. No. 9,346,601 B2, the entire contents of which are incorporated by reference herein.

FIELD OF THE INVENTION

The present invention relates to methods and packages for storing film strips while reducing or eliminating stress cracking during storage.

BACKGROUND OF THE INVENTION

Sporadic events of stress cracking in polymeric based film strips found in finished products but not observed in a 15 minute in-process check or AQL testing has been an issue with some polymeric based film products. Stress cracking generally begins to appear in the film product 2 to 4 weeks after manufacturing and packaging. Data analysis on lots exhibiting cracking has led to the conclusion that the problem is probably caused by imparting stress to the strips during the manufacturing process.

One source of stress that is imparted to the film during manufacturing is in the drying process. During drying, the wet film product is applied or coated to a substrate, and is then dried on that substrate. In some drying processes, particularly those including high solvent content, up to 70% of the volume of the wet film solution is removed in the drying process. This shrinkage imparts stress to the film, which adheres to the substrate onto which it is cast and dried. Another source of stress involves the cutting process. Following the initial drying and shrinkage, typically the film product is cut into individual rolls or strips. The film undergoes a number of bending operations as it transits the tortuous path of a slitting operation.

Finally, during fabrication and packaging of individual film strips, the process imparts additional stress by multiple turns around rollers, stripping the film off the substrate and by the pull wheels used to move the film product through the converting/packaging machine. When the strip is individually packaged in a material with a high surface energy, the film sticks to the packaging material and is not allowed to move to relieve the stresses. The stresses are thus relieved at a later time by stress cracking.

SUMMARY OF THE INVENTION

In one embodiment, the present invention provides methods for reducing or substantially reducing stress cracking of polymers in film products, such as edible film products including an active, by lowering the surface energy of packaging materials.

In one embodiment, the present invention provides methods for reducing or substantially reducing stress cracking of polymers in film products, such as edible film products including an active, such as a pharmaceutical active, by annealing the film prior to storing it in a pouch or package.

In one embodiment, the present invention provides methods for reducing or substantially reducing stress cracking of polymers in film products, such as edible film including an active, such as a pharmaceutical active, by annealing the pouch or package containing the film.

In one embodiment, the present invention provides methods for reducing or substantially reducing stress cracking of polymers in film products, such as edible film including an active, such as a pharmaceutical active, by both lowering the surface energy of packaging materials and by annealing the film prior to storing it in a pouch or package.

In one embodiment, the present invention reduces or substantially reduces stress cracking of polymers in film products, such as edible film including an active, such as a pharmaceutical active, by both lowering the surface energy of packaging materials and by annealing the pouch or package in which the film product is stored.

In one embodiment, there is provided a package for storing a film product including an active, such as a pharmaceutical active, including: (a) a top layer having an inner surface and an outer surface; and (b) a bottom layer having an inner surface and an outer surface, the top layer and/or the bottom layer including a polymeric material, the inner surface of the top layer and/or the inner surface of the bottom layer having reduced adhesion to a film product, such as a film; wherein the inner surface of the top layer is partially sealed to the inner surface of the bottom layer, wherein a pocket is formed between the top layer and the bottom layer, and wherein a film product such as a film is stored within the pocket. Without wishing to be bound by any theory, the inner surface of the top layer and/or the inner surface of the bottom layer has reduced adhesion to the film strip due to having (i) a surface energy measured by a water contact angle test of about 100 degrees or greater; and/or (ii) a surface adhesivity level of less than about 0.25 lbf as measured by a peel force testing using a load frame and 1 inch wide packaging tape pulled at 2 inches/minute and averaged over a distance of 0.75 to 1.75 inches; and/or (iii) a surface RMS roughness of less than 800 nm as measured by atomic force microscopy at a 100 micron square sample size square level.

In one embodiment, there is provided a package for storing pharmaceutical active containing film product, including: (a) a top layer having an inner surface and an outer surface; and (b) a bottom layer having an inner surface and an outer surface, the inner surface of the bottom layer including at least one polymeric material having at least one physical characteristic selected from the group consisting of: (i) a surface energy measured by a water contact angle test of about 100 degrees or greater; (ii) a surface adhesivity level of less than about 0.25 lbf as measured by a peel force testing using a load frame and 1 inch wide packaging tape pulled at 2 inches/minute and averaged over a distance of 0.75 to 1.75 inches; and (iii) a surface RMS roughness Root Mean Square (RMS) of less than 800 nm as measured by atomic force microscopy at a 100 micron square sample size level; where the inner surface of the top layer is partially sealed to the inner surface of the bottom layer, forming a pocket between the top layer and the bottom layer.

In one embodiment, there is provided a method for reducing or preventing stress-cracking in a film product, including: providing a package for storing pharmaceutical active containing film product, including: (a) a top layer having an inner surface and an outer surface; and (b) a bottom layer having an inner surface and an outer surface, at least partially sealing the inner surface of the top layer to the inner surface of the bottom layer to form a pocket therebetween, wherein the inner surface of the bottom layer includes at least one polymeric material having at least one physical characteristic selected from the group consisting of: (i) a surface energy measured by a water contact angle test of about 100 degrees or greater; and/or (ii) a surface adhesivity level of less than about 0.25 lbf as measured by a peel force testing using a load frame and 1 inch wide packaging tape pulled at 2 inches/minute and averaged over a distance of 0.75 to 1.75 inches; and/or (iii) a surface RMS roughness of less than 800 nm as measured by atomic force microscopy at a 100 micron square sample size level.

In one embodiment, there is provided a method for reducing stress cracking in a film including a continuous and uniform product including the steps of:
 (a) preparing a film-forming matrix including a solvent, an active and a polymeric material;
 (b) forming a dried film by casting the film-forming matrix and drying the film-forming matrix;
 (c) annealing the dried film to relieve stresses imposed by the drying process.

In one embodiment, there is provided a method for reducing stress cracking in a film, such as a film including a continuous and uniform product, including the steps of:
 (a) preparing a film-forming matrix including a solvent, an active and a polymeric material;
 (b) forming a dried film by casting the film-forming matrix and drying said film-forming matrix;
 (c) packaging the dried film in a pouch
 (d) annealing the pouched film to relieve stresses imposed by the drying process.

In one embodiment, there is provided a reduced stress cracked film product, such as a continuous and uniform film product, with reduced stress cracking, wherein the film product is formed by: casting a film-forming matrix including a solvent, an active, and a polymeric material, drying the film-forming matrix to form a dried film, and annealing the dried film to relieve stress imposed by the drying process. The film product has reduced stress cracking when the film is annealed compared to when the film is not annealed.

In one embodiment, there is provided a reduced stress cracked film product, such as a continuous and uniform reduced stress cracked film product, wherein the film product is formed by: casting a film-forming matrix and drying the film-forming matrix to form a dried film; packaging the dried film into a pouch, and annealing the pouched film to relieve stresses imposed by the drying process. The pouched film has reduced stress cracking when the film is annealed compared to when the film is not annealed.

In one embodiment, there is provided a pouch for storing a film product including an active, such as a pharmaceutical active, including a laminate of at least one first layer and at least one second layer, wherein the at least one first layer has an inner surface and an outer surface; wherein the second layer is positioned over the first layer; wherein the pouch includes a cavity including a film such as an edible film including at least one polymer and including at least one active, such as a pharmaceutical active, positioned therein, and wherein the pouch is laminated. The pouch may be made from any suitable material, including suitable polymeric materials. The film is annealed to prevent and/or reduce stress cracking in the film contained therein by applying heat to the film. Thereafter, the film may be placed and stored in a pouch or package in accordance with the present invention.

In one embodiment, there is provided a pouch for storing a film product including an active, such as a pharmaceutical active, including a laminate of at least one first layer and at least one second layer, wherein the at least one first layer has an inner surface and an outer surface; wherein the second layer is positioned over the first layer; wherein the pouch includes a cavity including a film which has been annealed, such as an edible film which has been annealed and which includes at least one polymer and including at least one active, such as a pharmaceutical active, positioned therein, and wherein the pouch is laminated. The pouch may be made from any suitable material, including suitable polymeric materials.

In one embodiment, there is provided a method for reducing stress cracking in a film product comprising: (a) providing a sealed pouch including a laminate of at least one first layer and at least one second layer, wherein the at least one first layer has an inner surface and an outer surface; wherein the at least one second layer has an inner surface and an outer surface; wherein the second layer is positioned over said first layer; and wherein the pouch includes a cavity including an edible film including at least one polymer and an active, such as a pharmaceutical active, positioned therein, and (b) annealing the pouch to prevent and/or reduce stress-cracking in the film by applying heat to the pouch.

DETAILED DESCRIPTION OF THE INVENTION

Figure 1:
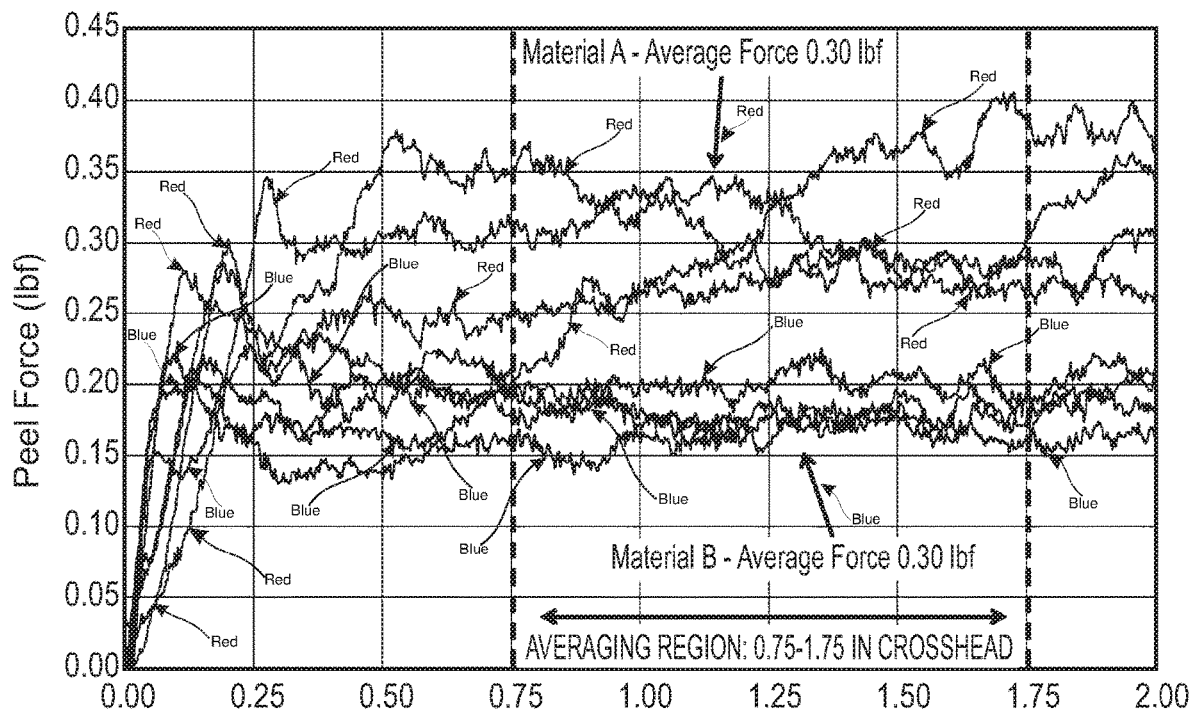
FIG. 1 shows the results of a comparative foil film peel test.

As used herein, the term "annealing" means a heat treatment that alters a material to, among other things, relieve internal stresses.

As used herein, the term "stress cracking" means a phenomena occurring in polymers, where the material is held together by a combination of weaker Van der Waals forces and stronger covalent bonds. When sufficient local stress overcomes the Van der Waals force, a gap is formed resulting in a stress crack. These stress cracks can start as minute cracks, visible only under a microscope and depending on the stress in the polymer, can with time separate a polymer film into 2 or more pieces. If the polymer film is left unrestrained, the stresses will relieve themselves when the film is allowed to shrink. However, when the film is restrained by adhesion to a surface, the film cannot shrink and will subsequently crack. Stress can also be relieved by annealing, which allows relaxation of the stresses in the polymer and therefore prevents stress cracking.

As used herein, the terms "pharmaceutical", "medicament", "drug" and "active" may be used interchangeably, and refer to a substance or composition useful for the prevention or treatment of a condition. The terms may include pharmaceuticals, neutraceuticals, cosmetic agents, biologic agents, bioeffective substances, and the like.

It will be understood that the terms "film" and "film strip" include delivery systems of any thickness, including films and film strips, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the processing of the film. Films may include a pouch or region of medicament between two films. The films of the present invention may have any desired dimension suitable to provide the desired level of active, and in some embodiments, the films have a length from about 10 to about 50 mm and a width of from about 10 to about 50 mm, and may take any desired shape, including square and rectangle.

The term "patch" as used herein is intended to include multi-layered film products, where the first layer (or "backing layer") is a film product that has a slower rate of dissolution than the second layer (or "active layer"). Patches described herein generally include the first and second layers adhered or laminated to each other, where the second layer has a smaller length and/or width of the first layer, such that at least a portion of the surface of the first layer is visible outside of the second layer.

Film strips may be formed through any desired processing means, including casting and drying methods as well as extrusion methods. The film strips may be single-layer films or multiple layered films. Some examples of methods of forming and drying films may be found in U.S. Pat. Nos. 7,425,292, 7,666,337, and 7,357,891, the contents of each of which are incorporated by reference in their entireties. Any number of active components or pharmaceutical agents may be included in the films discussed herein. The active component(s) may be disposed within any layer of film products formed herein or they may be placed onto one or more surfaces of the film products.

Films formed by the present invention may be suitable for administration to at least one region of the body of the user, such as mucosal regions or regions within the body of the user, such as on the surface of internal organs. In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), ocular and anal areas of the body. In still other embodiments, the topical agent is applied to an internal organ or other body surface of the user, such as during surgery, where the agent may be removed or left within the body after surgery is complete. In other embodiments, a topical agent is applied to a hard surface, such as a particular surface area in need of treatment. In other embodiments, the films of the present invention are ingestible, and are intended to be placed in the mouth of the user and swallowed as the film disintegrates.

The medicament may be dispersed throughout the film, or it may be deposited onto one or more surfaces of the film. In either way, it is desirable that the amount of medicament per unit area is substantially uniform throughout the film. The "unit area" is intended to include a suitable unit area, such as the area of one typical dosage unit. It is desired that the films of the present invention include a uniformity of component distribution throughout the volume of a given film. That is, the individual film products (including individual dosages of approximately equal sizes) formed by the present invention should have approximately the same content composition as each other film product. Such uniformity includes a substantially uniform amount of medicament per unit volume of the film, whether the medicament is within the matrix of the film or coated, laminated, or stabilized on one or more surfaces thereof. When such films are cut into individual units, the amount of the agent in the unit can be known with a great deal of accuracy. For the films formed herein, it is understood by one of ordinary skill in the art that the resulting film is not required to be exactly 100% uniform. All that is required is that the film be "substantially uniform", i.e., a slight amount of non-uniformity is understood to be acceptable. "Substantially uniform" may include, for example, a film that is about 90% uniform in content from one region of the film to another, or a film that is about 95% uniform in content from one region of the film to another, and most desirably about 99% uniform in content from one region of the film to another. In other words, "substantially uniform" may mean that individual film products should vary by no more than about 10% with respect to each other. In some embodiments, "substantially uniform" may mean that individual film products should vary by no more than about 5% with respect to each other.

After formation of the film, a plurality of film strips having similar dimensions, including length, width and depth, may be cut from the film product. Each film strip is desirably substantially uniform in content from each other, particularly in active content. When forming films, the user sets a target active content, depending upon the desired level of active in the film. That target content is referred to as 100% of the target level. For example, the desired film strip may desirably have 1 mg of active per unit dose, and thus 1 mg would be the "target content". Each substantially similarly sized film strip cut from the film product should be within about 10% of that target content. More desirably, each substantially similarly sized film strip cut from the film product should be within about 8% of the target content, or within 6% of the target content, or within 4% of the target content. For a target content of 1.0 mg per unit dose, substantially uniform films may have from about 0.90 mg to about 1.10 mg per unit dose. When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The active components that may be incorporated into the films of the present invention include, without limitation pharmaceutical and cosmetic actives, drugs, medicaments, proteins, antigens or allergens such as ragweed pollen, spores, microorganisms, seeds, mouthwash components, flavors, fragrances, enzymes, preservatives, sweetening agents, colorants, spices, vitamins and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulants, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs or other preferred active ingredients for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and $Ca^H$-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono- or di-basic calcium phosphate, tricalcium phosphate, potassium bicarbonate, sodium tartrate, sodium bicarbonate, magnesium aluminosilicates, tartaric acids and salts. The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide. Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components. Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The film products of the present invention are capable of accommodating a wide range of amounts of the active ingredient. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

Sweeteners for use in the present invention may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

The film products and methods of the present invention are well suited for high potency, low dosage drugs. This is accomplished through the high degree of uniformity of the films. Therefore, low dosage drugs, particularly more potent racemic mixtures of actives are desirable. The polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100L, believed to be 100% lactide having a melting point within the range of 338°–347° F. (170°–175° C.); lactide/glycolide 100L, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC).

Desirably, the films of the present invention include polyethylene oxide (PEO), hydroxypropylmethylcellulose or a combination thereof.

The layers of the packages and pouches of the present invention may include any suitable packaging material. Desirably, low density polyethylene (LDPE) and/or ethylene acrylic acid may be product contact layers in packaging material. Once a film strip is formed and cut to the appropriate and desired size, the film strip is packaged. Packaging of film strips helps keep the film strips in a controlled environment so as to maintain the integrity of the film strip and the active content. Desirably, a single package houses one single film strip and is sealed so that the film strip is not exposed to an external environment. Typically, film strip packages are made from foil, polymeric materials, or combinations of foil and polymeric materials. In some embodiments, the package is made from at least one laminated foil, where the foil is laminated with a polymeric material. The package is capable of being opened by the user by one or more known methods, including, for example, tear notches, perforations, or through use of a tool such as scissors or other blade.

Figure 5:
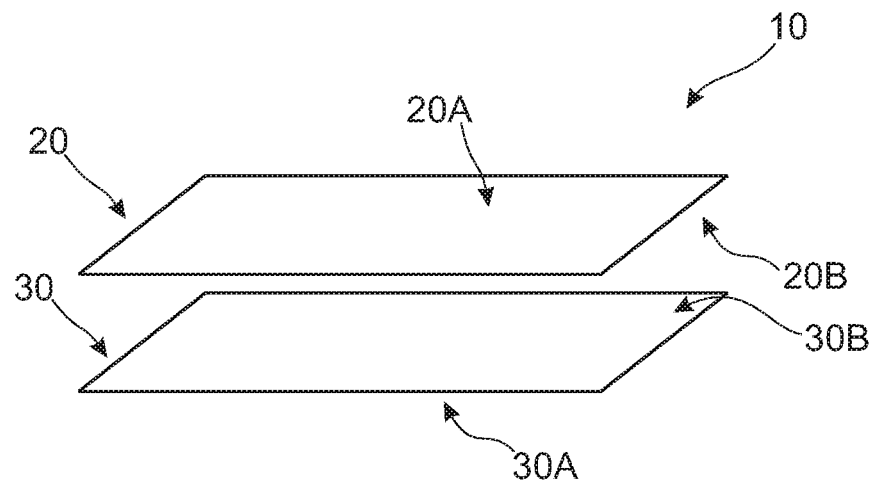
FIG. 5 shows layers for use in forming a package or pouch of the present invention.
Figure 6:
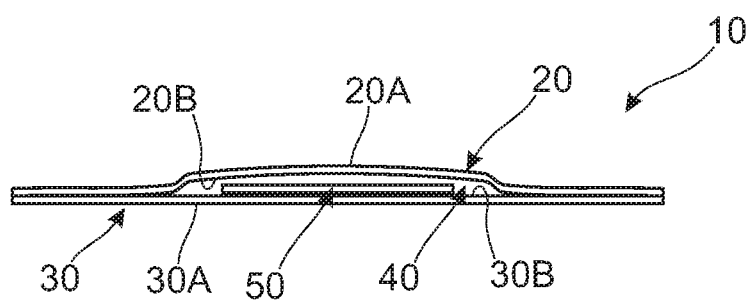
FIG. 6 is a cross sectional view of a package of the present invention.

A representative package suitable for the present invention is shown in FIG. 6. A top layer 20 including an outer surface 20A and a bottom surface 20B and a bottom layer 30 including an outer surface 30A and an inner surface 30B for use in making the package are shown in FIG. 5. As shown in FIG. 6, the package 10 includes a top layer 20 and bottom layer 30. The top layer 20 includes an outer surface 20A that is exposed to the outside environment, and an inner surface 20B that is in contact with an interior pocket 40 of the package 10. The bottom layer 30 also includes an outer surface 30A that is exposed to the outside environment and an inner surface 30B that is in contact with the interior pocket 40 of the package. A film strip 50 is contained within the interior pocket 40 of the package 10. The package 10 may be oriented in any direction, but for ease of explanation FIG. 6 shows the bottom layer 30 under the top surface 20, such that the film strip 50 rests on the inner surface 30B of the bottom layer 30. It is understood that in some embodiments, the film strip 50 may be in at least partial contact with the inner surface 20B of the top layer 20. Since the film strip 50 is or may be in contact with the inner surfaces 20B, 30B of the package 10, the inner surfaces 20B, 30B of the package 10 should be made from a material or materials that are inert with respect to the film strip 50. The materials forming the inner surfaces 20B, 30B of the package 10 should not be capable of reacting with the film strip 50 so as to affect the film strip 50 in a material way.

After cutting the film strip to the proper and desired size, it is placed onto the inner surface 30B of the package 10, and the package 10 is then closed around the film strip 50 and sealed. The film strip 50 may remain in the package 10 for an extended period of time, and may be within the package 10 for days, weeks, months, or even years. In some embodiments, the package 10 is suitable to house the film strip 50 without detrimental damage to the film strip 50 for at least 1 week, or for at least 1 month, or for at least 6 months, or for at least 1 year. In some embodiments, the film strip 50 suitably remains in the package 10 for about 1 month to about 2 years without detrimental damage. In some embodiments, the film strip 50 suitably remains in the package 10 for about 1 month to about 2 years without detrimental damage.

In some embodiments, the film may be formed directly onto the inner surface of the package during the manufacturing stage. In such embodiments, the film strip is formed at the desired dimensions, smaller than the package.

When a user wishes to use the film strip, the user opens the package and removes the film strip. It is important that the film strip not stick to or adhere to the inner surface of the package, so as to allow for easy removal of the film strip. However, in addition to the ease of removal of the film strip, the present inventors have discovered that the inner surface of the package should be made from a material that resists formation of stress cracking in the film strip. This is particularly true when the film strip is made from a polymeric material or materials that are susceptible to stress cracking. As will be discussed below, the inner surface of the package desirably is made from a material or materials having a low surface energy. In addition, the inner surface may have a lower surface adhesivity with respect to the film strip that is housed in the package. Also, or in the alternative, the inner surface may have a lower root mean square surface roughness, as measured at the 100 micron square sample size scale. Each of these properties is discussed below.

Stress cracking of films is particularly noticeable when certain polymers are used in the film product. Such polymers include polymers that are or can become highly crystalline in nature. One particularly noticeable polymer that causes stress cracking is polyethylene oxide (PEO). However, polymeric materials such as PEO offer a number of advantages in a film product, and thus it is desirable to use PEO and similar materials, either alone or in combination with other polymeric components, in the formation of films. For example, PEO may be used in combination with a cellulosic material, such as HPC or HPMC. Unfortunately, due to its tendency to cause stress cracking, PEO has been found to cause problems when the user wishes to use the film. As such, certain measures should be taken during the preparation and packaging of the film strips. One such measure is to use packaging materials that include an inner surface made from a material or materials that will reduce the likelihood of stress cracking. Desirable materials include those that have at least one of the following characteristics: the inner surface of the package being made from a material or materials having a low surface energy; the inner surface having a lower surface adhesivity with respect to the film strip that is housed in the package; and the inner surface having a lower root mean square surface roughness, as measured at the 100 micron square sample size scale.

It has been noticed by the present inventors that films including PEO as either the sole or as one of the polymeric materials in the film can suffer from stress cracking. Such films have suffered from stress cracking even on a number of different packaging materials. Stress cracking is undesirable as it has an unappealing appearance, thus causing the user of the film strip to question its integrity and usefulness. The present inventors have noticed that films including PEO as a polymeric component tended to adhere to various packaging materials, thus causing more stress cracking as observed when the package was opened. One such packaging material that demonstrated noticeable stress cracking in films was a material having an inner surface made from ethylene acrylic acid. Up to 63% of films that were prepared on such packaging materials demonstrated stress cracking.

The present inventors have discovered, however, that a film including polymers that are or can become highly crystalline in nature as a polymeric component can be formed without stress cracking when stored on a packaging material made from a material having a lower surface energy, having lower surface adhesivity, or having a lower surface roughness. The surface energy of a product may be measured by a water contact angle test, described below. The desired surface energy is about 100 degrees or greater, as measured by the water contact angle test.

Surface adhesivity may be measured by peel force testing using a load frame and packaging tape. Using such a test, the desired surface has an average peel force of less than about 0.25 lbf, and more desirably less than about 0.20 lbf. Finally, surface RMS roughness may be measured by atomic force microscopy at a 100 micron square sample size level. At the 100 micron square sample size level, the desired surface RMS roughness of the package material should be less than about 800 nm, and desirably less than about 700 nm.

One such packaging material having a lower surface energy includes materials made from low density polyethylene (LDPE). When the inner surface of the package is made from a material including LDPE, the film strips were found to have reduced or eliminated stress cracking. Such inner surfaces have a surface energy of about 100 degrees or greater as measured by the water contact angle test, a surface adhesivity of about 0.25 lbf or less as measured by peel force testing, and a surface RMS roughness of about 800 nm or less as measured by atomic force microscopy at a 100 micron square sample size level.

Desirably, less than 10% of film strips stored in the inventive package exhibit stress cracking after storage of about three months at temperatures of about 25° C. to about 30° C.

Surface roughness was measured using Atomic force microscopy (AFM). AFM scans were completed with three scans of each film, one 100 μm square, one 25 μm square, and one 5 μm square. As the scan size decreases, the lateral resolution of the images increases, allowing the small scan sizes to make out smaller features.

Water contact angle tests were conducted by applying a 5 microliter drop of purified water on the film using a micro-pipette. Images were taken of each drop and image processing was used to capture the shape of each drop's surface, and the data was processed to calculate the contact angle.

Peel tests were conducted with packaging tape applied to sampled films. Test samples were one inch wide. The ends of the tape and the substrate films were clamped by grips of an MTS load frame (tensile tester), manufactured by MTS Systems Corporation. The tests were run at 2 inches per minute speed. The load rises as the specimen ends are pulled until the sample is taught and peeling progresses. Once peeling is initiated, the load is variable, based on the local bond strength between packaging tape and the substrate film. The data became more stable after a moderate opening length, and the test data was averaged over on opening distance of 0.75 inches to 1.75 inches.

In some embodiments, additives may optionally be included in the films of the present invention to assist in ameliorating internal stresses in the film structure. Such additives may include, for example, surfactants, plasticizers, and vitamin E, TPGS, and combinations thereof. Such additives may be present in any suitable amount. Suitable amounts of such additives include, for example, from about 1% by weight to about 50% or higher by weight of a film. In some embodiments, a plasticizer may be present in an amount from about 5% by weight to about 30% by weight of a film. In some embodiments, a plasticizer may be present in an amount from about 2% by weight to about 30% by weight of a film. In some embodiments, a plasticizer may be present in an amount of about 5% by weight of a film.

The present invention also reduces the tendency and likelihood of stress cracking through certain measures taken in the packaging stage of formation.

In some embodiments, a film may be annealed to reduce or substantially reduce stress cracking in the film prior to being stored in a package or pouch. In some embodiments, a film is annealed at a temperature between 40 degrees C. and 90 degrees C. In some embodiments, the film is annealed at a time between 0.5 minutes and 60 minutes.

In some embodiments, a film is annealed by removing the film from a substrate, annealing the film and rewinding the film onto a substrate. In some embodiments, a film is annealed at a temperature between 40 degrees C. and 90 degrees C. In some embodiments, a film is annealed at a time between 0.5 minutes and 60 minutes. In some embodiments, a film is intact with no cracking after 3 weeks in a package.

In some embodiments, a film is intact with no cracking after 2 months in a package. In some embodiments, a film is intact with no cracking after 6 months in a package. In some embodiments, a film is intact with no cracking after 12 months in a package. In some embodiments, a film is intact with no cracking after 2 years in a package. In some embodiments, a film is intact with no cracking after 3 years in a package. In some embodiments, a film is intact with no cracking after 3 weeks in a package. In some embodiments, a film is intact with no cracking after 2 months in a package. In some embodiments, a film is intact with no cracking after 6 months in a package. In some embodiments, a film is intact with no cracking after 12 months in a package. In some embodiments, a film is intact with no cracking after 2 years in a package. In some embodiments, a film is intact with no cracking after 3 years in a package.

In some embodiments, a package or pouch including a film product, such as a polymeric film, may be annealed to prevent and/or reduce stress-cracking in the film. In some embodiments, the package or pouch including the product is annealed by placing the sealed pouches of the product in an oven. The package or pouch may be heat annealed for any suitable length of time, including from about 0.5 to about 120 minutes. Moreover, the package or pouch may be annealed at any suitable temperature, including from about 40° C. to about 90° C. In some embodiments, the packaged film is annealed at a temperature between 40 degrees C. and 90 degrees C.

Desirably, a package or pouch of the present invention is heat annealed at 70° C. for 25 minutes. In some embodiments, a packaged film is annealed at a time between about 0.5 minutes and about 60 minutes. In some embodiments, a packaged film is annealed at a time between 0.5 minutes and 60 minutes.

EXAMPLES

Example 1—Comparative Testing Between Two Materials

Two materials were tested for peel force using a load frame and packaging tape. The first material ("Material A") was a packaging product having a surface made from ethylene acrylic acid, and the second material ("Material B") was a packaging product having a surface made from LDPE. FIG. 1 demonstrates the foil film peel test results for these two materials.

Test samples were one inch wide. The ends of the tape and the substrate films were clamped by grips of an MTS load frame. The tests were run at 2 inches per minute speed. The load rises as the specimen ends are pulled until the sample is taught and peeling progresses. Once peeling is initiated, the load is variable based on the local bond strength between packaging tape and the substrate film. The data became more stable after a moderate opening length, and the test data was averaged over on opening distance of 0.75 inches to 1.75 inches.

Water contact angle tests were then run on the surfaces of the two materials. These tests were conducted by applying a 5 microliter drop on the product contact surface using a micro-pipette. Images were taken of each drop, and image processing was used to capture the shape of each drop's surface, and the data was processed to calculate the contact angle.

Film contact angle results show that Material B, having a surface made from LDPE, demonstrated the highest contact angle and therefore the lowest surface energy of the materials tested. The higher surface energy of Material A (having a surface made from ethylene acrylic acid) results in better wet-out and a greater tendency for other materials (e.g. film strips) to stick to the surface. This is again consistent with observations that film strips tend to stick to Material A. The results are set forth in Table 1 below:

TABLE 1

Film Contact Angle Results

| Sample | Contact Angle (deg) | | | | | |
|---|---|---|---|---|---|---|
| Material A | 95.6 | 95.4 | 88.9 | 89.2 | 88 | 89.3 |
| Material B | 100.7 | 104.7 | 106.8 | 109.5 | 109.2 | 106.3 |

Figure 2:
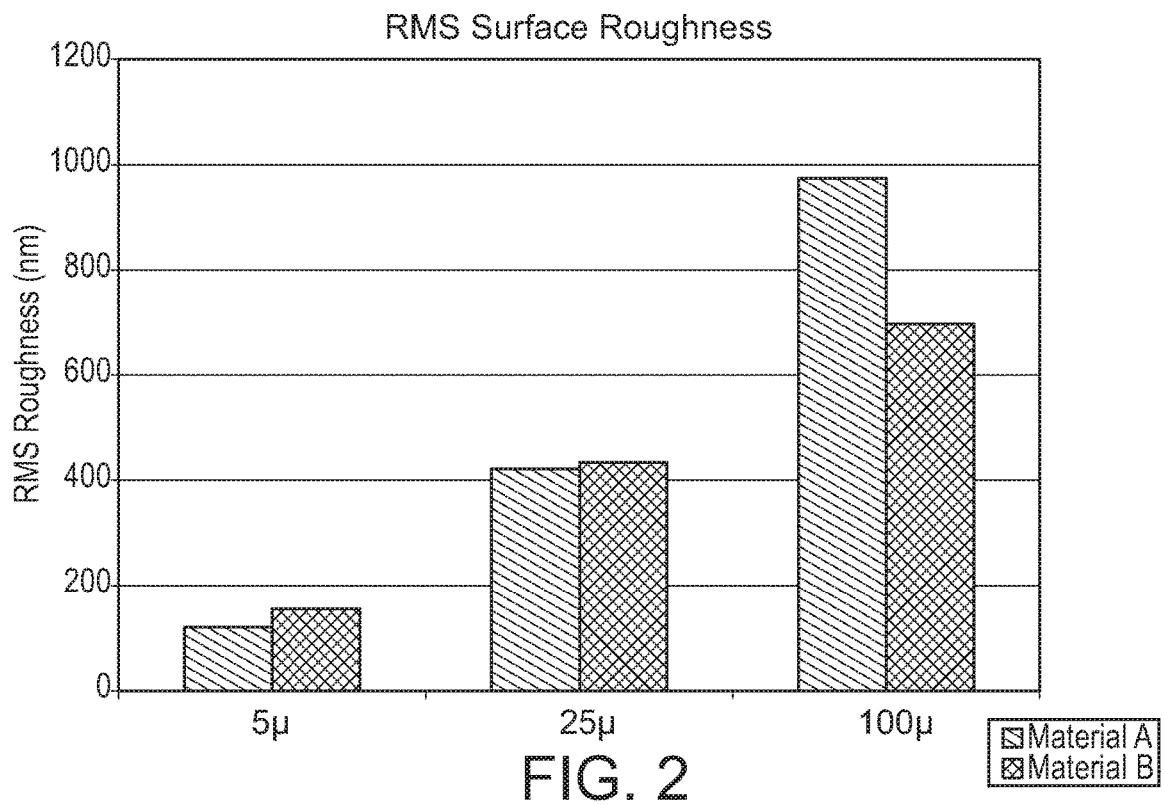
FIG. 2 shows the results of an AFM surface RMS roughness test for various films.

Atomic force microscope (AFM) scans were completed on both films to gain additional insight into the physical structure of each. Three scans of each film, one 100 μm square, one 25 μm square, and one 5 μm square were done. As the scan size decreases, the lateral resolution of the images increases, allowing the small scan sizes to make out smaller features. FIG. 2 shows the AFM surface RMS roughness of the films.

The results indicate that at the 100 micron square same size scale, the Material A shows the highest surface roughness, approximately 30% more rough than Material B. This is consistent with the Material A having higher surface energy and higher adhesivity to other materials. The data then can be summarized as the peel force testing, contact angle measurement and surface RMS roughness measurements by AFM all suggest that the Material A packaging material has a higher surface adhesivity (peel force), a higher surface energy (lower contact angle) and a higher surface RMS roughness at a 100 micron square sample size scale.

These results are consistent with observations that film strips are often found sticking to Material A when opened for examination. It is believed that this tendency to stick to Material A is directly related for the film strips' tendency to crack while in the Material A package. The results are also consistent with the observation that the film strips have seldom been found to stick to the Material B and the strips experience much less stress cracking when packaged in this material. Since Material B has a lower surface energy and roughness, the strips do not tend to stick and subsequently crack when packaged into this material.

Example 2—Comparative Testing

Two lots of film product, both including PEO as a polymeric component, were manufactured and packaged in two separate packaging materials. The first packaging material included an inner surface made from ethylene acrylic acid and the second packaging material included an inner surface made from LDPE. These lots were inspected after 20 weeks for stress cracked strips.

After twenty weeks, the first lot packaged in the ethylene acrylic acid packaging showed 30.4% stress cracking, and the first lot packaged in the LDPE packaging showed 4.2% stress cracking. Also after twenty weeks, the second lot packaged in the ethylene acrylic acid packaging showed 46.4% stress cracking, and the first lot packaged in the LDPE packaging showed 0% stress cracking.

Example 3—Use of LDPE Packaging Material

Five lots of film material, each including PEO as a polymeric component, were packaged in a packaging material including an inner surface made from LDPE and placed in a 36 month stability program. The samples were stored at either 25° C. or 30° C. At the end of the 36 months, samples were inspected for stress cracking. The results are presented in Table 2 below:

TABLE 2

Stress cracking after 36 months storage at different temperature conditions.

| Lot No. | Number of Samples | Storage temperature (° C.) | Percentage with Stress Cracking |
|---|---|---|---|
| 1 | 25 | 25 | 0% |
| 2 | 25 | 25 | 0% |
| 3 | 25 | 25 | 0% |
| 4 | 25 | 25 | 0% |
| 5 | 25 | 25 | 0% |
| 1 | 25 | 30 | 0% |
| 2 | 25 | 30 | 0% |
| 3 | 25 | 30 | 0% |
| 4 | 25 | 30 | 0% |
| 5 | 25 | 30 | 0% |

Example 4—Use of LDPE Packaging Material

Nine lots of three different strengths of film, each including PEO, were manufactured and packaged in a packaging material having an inner surface made from LDPE. The films were inspected for stress cracking after 5 months. The results are shown in Table 3 below:

TABLE 3

Frequency of stress cracking in experimental lots.

| Lot No. | Percentage with Stress Cracking |
|---|---|
| 1 | 0% |
| 2 | 0% |
| 3 | 0% |
| 4 | 0% |
| 5 | 0% |
| 6 | 0.67% |
| 7 | 0.20% |
| 8 | 0% |
| 9 | 0% |

Example 5—Comparative Testing

Twelve lots of film, each including PEO as a polymeric component, were packaged in a packaging material having an inner surface made from ethylene acrylic acid, and thirty-three lots were packaged in a packaging material having an inner surface made from LDPE. The films were all inspected after 3 weeks for stress cracking. The two populations were then compared using a 2 sided test. The results are shown in Table 4. The value of 0.005 for p indicates a high probability the data sets are different populations.

TABLE 4

Results of t test on populations

| Packaging Material | | Defect Rate |
|---|---|---|
| Ethylene acrylic acid | Mean | 8.38% |
| | SD | 6.3% |
| LDPE | Mean | 2.01% |
| | SD | 1.4% |
| p | | 0.005 |

Example 6—Comparative Testing

Figure 3:
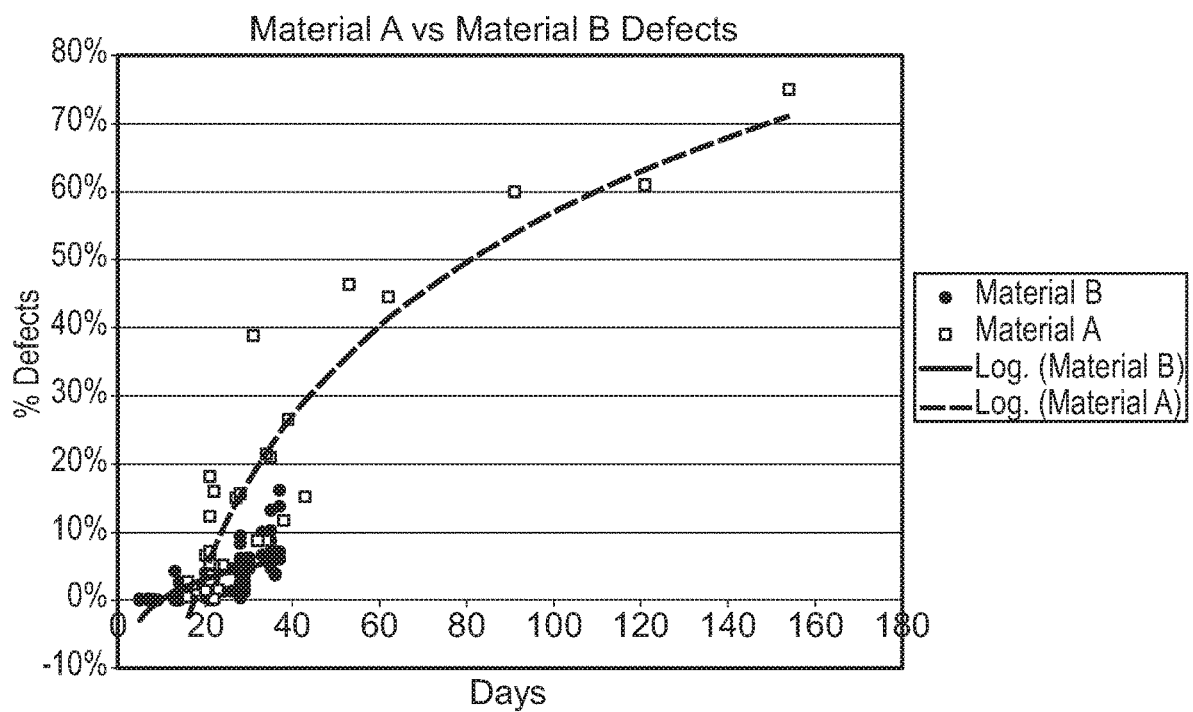
FIG. 3 shows the rate of stress cracking of films at various times.
Figure 4:
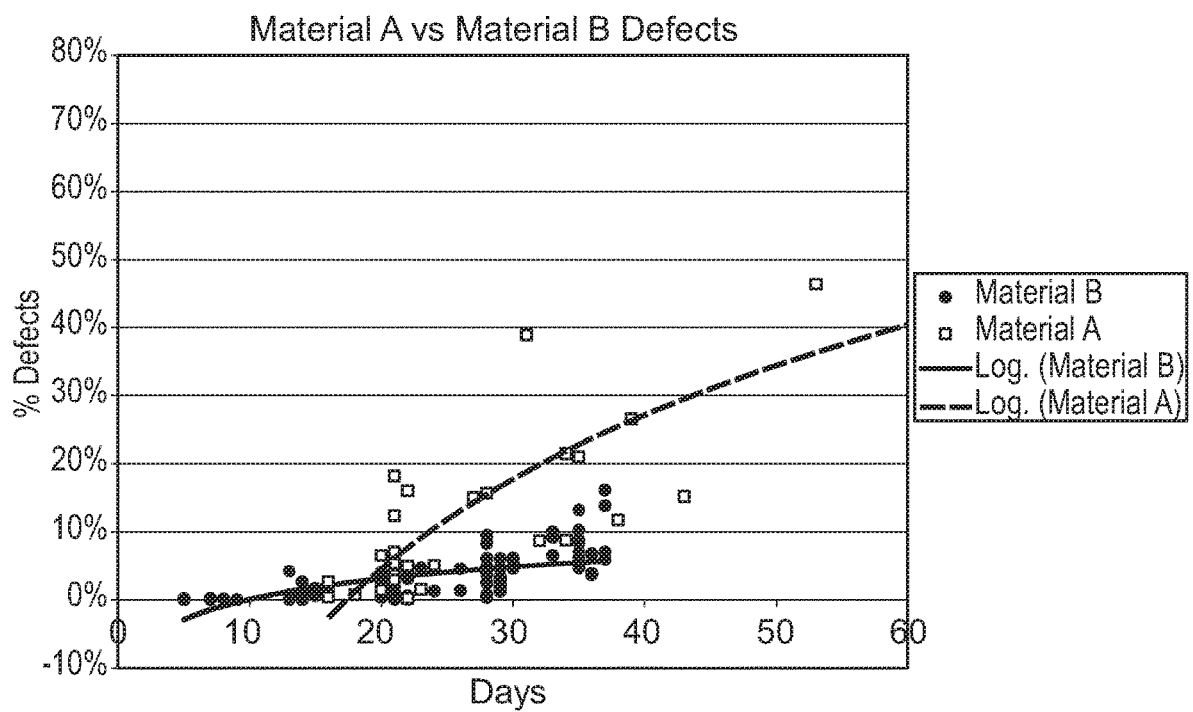
FIG. 4 shows the rate of stress cracking of films after a sixty day period.

Samples from 22 lots of film, all including PEO as polymeric component, were packaged in a packaging material including an inner surface made from ethylene acrylic acid and samples from 32 lots of film, each including PEO as polymeric component, were packaged in a packaging material including an inner surface made from LDPE. The films were inspected at different times after packaging. The data is shown in FIG. 3. To more clearly differentiate the rate of stress cracking at the earlier times, a second plot (FIG. 4) shows data obtained after 60 days.

Example 7

Film strips were individually packaged in foil/PET laminate pouches. Some of the product was heat annealed by placing the sealed pouches of product in an oven at 70 degrees ° C. for 25 minutes. The product was then inspected over time for stress cracking. For each week (post packaging) 2000 samples were opened and inspected. The results are shown in Table 5.

TABLE 5

Comparison of stress cracking in annealed and not annealed film

|  | Week 2 | Week 3 | Week 4 |
|---|---|---|---|
| Lot A, not annealed | 0.9% | 3.3% | 4.0% |
| Lot A, annealed | 0.00% | 0.00% | 0.00% |
| Lot B, not annealed | 1.0% | 8.4% | 5.7% |
| Lot B, annealed | 0.25% | 0.00% | 0.00% |

Based upon the data in Table 5, it is apparent that not annealed material consistently has more stress cracking than the annealed product, which exhibits essentially no stress cracking or minimal stress cracking.

Example 8

Figure 7:
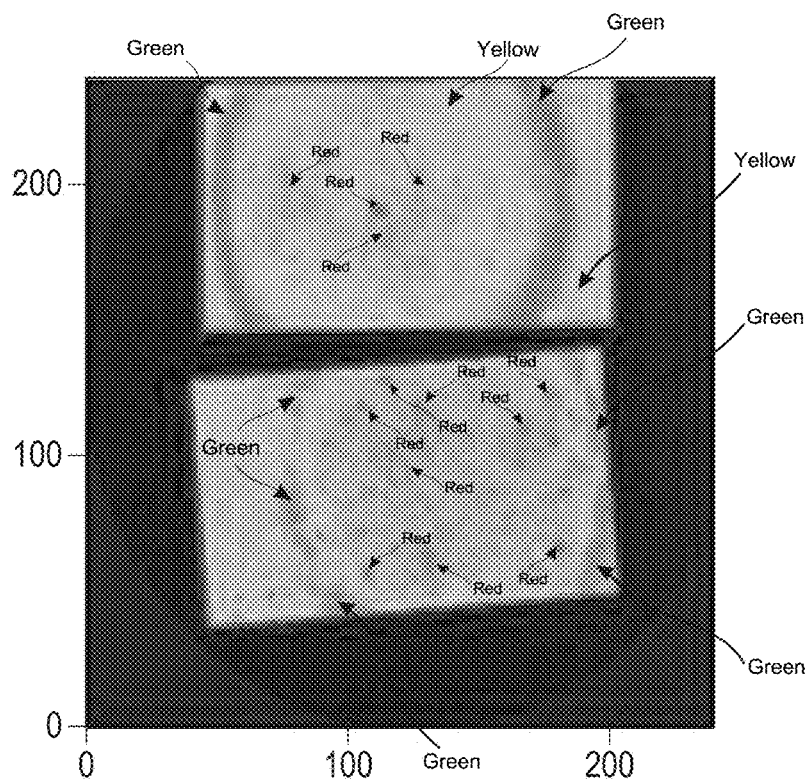
FIG. 7 is a 2D birefringence map of a "fresh" (1 week old) film strip (shown at the top of FIG. 7) and "old" (3 week old) film strip (shown at the bottom of FIG. 7) before anneal.
Figure 8:
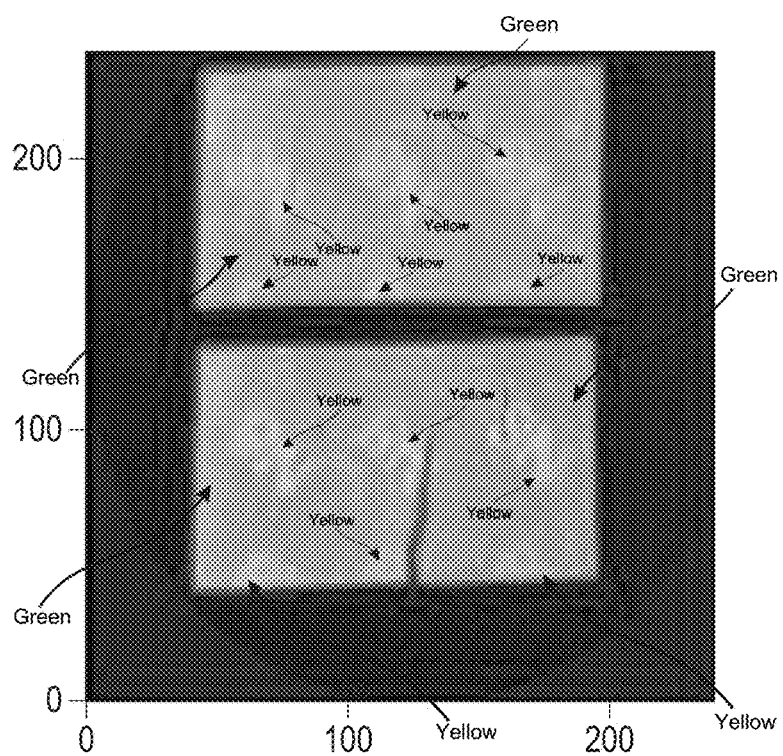
FIG. 8 is a 2D birefringence map of a "fresh" (1 week old) film strip (shown at the top of FIG. 8) and "old" (3 week old) film strip (shown at the bottom of FIG. 8) after anneal.

Fresh (1 week old) and old (3 month old) of individual film strips packaged in a foil/PET laminate pouch were examined using a Hinds near infrared birefringence systems using a measurement wavelength of 1310 nanometers. This wavelength surprisingly showed anisotropic and isotropic changes while other birefringence instruments and wavelengths were not able to see any birefringence. Mild heating at 70° C. for 1 hour surprisingly resulted in a complete reduction of the stress as is apparent from comparing the 2D birefringence map before anneal (top: Fresh, Bottom: Old) shown in FIG. 7 to the 2D birefringence map after anneal (top: Fresh, Bottom: Old) shown in FIG. 8. The yellow and red areas indicate higher internal stress while the green indicates the lowest stress. It is evident from this experiment that both old and fresh films exhibit internal stress before the annealing process and that heat annealing lowers the internal stress of both the fresh and old samples.

Example 9

A film in accordance with the present invention is coated onto a substrate and dried in accordance with drying methods as disclosed in U.S. Pat. Nos. 7,425,292, 7,666,337, and 7,357,891. Before, during or after slitting, the film is continuously delaminated from the substrate, heated to an annealing temperature, preferably 70 degrees C. (range of 40-90 degrees) for a period of 10 minutes (range 0.5-60 minutes) and rewound onto a substrate. The film is then cut and packaged on standard packaging machine into any type of packaging material.

What is claimed is:

1. A method for reducing or preventing stress-cracking in a film product, comprising:
   (1) providing a package for storing an active-containing film product, said package comprising:
      (a) a top layer having an inner surface and an outer surface; and
      (b) a bottom layer having an inner surface and an outer surface,
   wherein said inner surface of said bottom layer comprises at least one polymeric material having at least one physical characteristic selected from the group consisting of:
      (i) a surface energy as measured by a water contact angle test of about 100 degrees or greater; and
      (ii) a surface RMS roughness of less than about 800 nm as measured by atomic force microscopy at a 100 micron square sample size level;
   wherein said polymeric material has a surface adhesivity level of less than about 0.25 lbf as measured by a peel force test using a load frame and packaging tape; and
   (2) packaging a film product comprising an active within said package;
   wherein stress-cracking of said film product is prevented or reduced when said film product is packaged in said package.

2. The method of claim 1, wherein said active is a pharmaceutical active.

3. The method of claim 1, further comprising at least partially sealing said inner surface of said top layer to said inner surface of said bottom layer to form a pocket therebetween.

4. The method of claim 3, wherein said packaging of said film product within said package comprises packaging said film product within said pocket.

5. The method of claim 4, further comprising sealing said top layer to said bottom layer so as to provide a sealed pocket.

6. The method of claim 1, wherein said inner surface of said top layer comprises at least one polymeric material having at least one physical characteristic selected from the group consisting of:
   (i) a surface energy as measured by a water contact angle test of about 100 degrees or greater;
   (ii) a surface adhesivity level of less than about 0.25 lbf as measured by a peel force test using a load frame and packaging tape; and
   (iii) a surface RMS roughness of less than about 800 nm as measured by atomic force microscopy at a 100 micron square sample size level.

7. The method of claim 1, wherein said surface adhesivity level of said inner surface of said bottom layer is less than about 0.20 lbf as measured by a peel force test using a load frame and packaging tape.

8. The method of claim 1, wherein said surface RMS roughness of said inner surface of said bottom layer is less than about 700 nm as measured by atomic force microscopy at a 100 micron square sample size level.

9. The method of claim 6, wherein said surface adhesivity level of said inner surface of said top layer is less than about 0.20 lbf as measured by a peel force test using a load frame and packaging tape.

10. The method of claim 6, wherein said surface RMS roughness of said inner surface of said top layer is less than about 700 nm as measured by atomic force microscopy at a 100 micron square sample size level.

11. The method of claim 1, wherein said film product comprises polyethylene oxide.

12. The method of claim 11, wherein said film product further comprises a second polymeric material different from polyethylene oxide.

13. The method of claim 1, wherein said film product comprises less stress-cracking after twenty weeks in said package than a film product not packaged in said package.

14. The method of claim 1, wherein said film product shows 0% stress-cracking after twenty weeks in said package.

15. The method of claim 1, wherein said film product shows 0% stress-cracking after thirty-six months in said package.

16. The method of claim 1, wherein said film product shows 0% stress-cracking after five months in said package.

17. The method of claim 1, wherein said inner surface of said bottom layer comprises low density polyethylene.

18. The method of claim 1, wherein said inner surface of said top layer comprises low density polyethylene.

19. The method of claim 1, wherein said film product exhibits less stress-cracking than a film product packaged in a package comprising a packaging material having:
   (i) a surface energy as measured by a water contact angle test of less than about 100 degrees;
   (ii) a surface adhesivity level of greater than about 0.25 lbf as measured by a peel force test using a load frame and packaging tape; and
   (iii) a surface RMS roughness of greater than about 800 nm as measured by atomic force microscopy at a 100 micron square sample size level.

20. The method of claim 6, wherein said film product exhibits less stress-cracking than a film product packaged in a package comprising a packaging material having:
   (i) a surface energy as measured by a water contact angle test of less than about 100 degrees;
   (ii) a surface adhesivity level of greater than about 0.25 lbf as measured by a peel force test using a load frame and packaging tape; and
   (iii) a surface RMS roughness of greater than about 800 nm as measured by atomic force microscopy at a 100 micron square sample size level.

* * * * *